US 11,898,133 B2

(12) United States Patent
Zhang et al.

(10) Patent No.: US 11,898,133 B2
(45) Date of Patent: Feb. 13, 2024

(54) ORBITAL INCUBATOR SHAKERS

(71) Applicant: SHINETEK INSTRUMENT RESEARCH INSTITUTE, Beijing (CN)

(72) Inventors: Gongrun Zhang, Beijing (CN); Gongze Zhang, Beijing (CN); Zhiyong Jia, Beijing (CN); Chengxiang Zhang, Beijing (CN)

(73) Assignee: SHINETEK INSTRUMENT RESEARCH INSTITUTE, Beijing (CN)

( * ) Notice: Subject to any disclaimer, the term of this patent is extended or adjusted under 35 U.S.C. 154(b) by 361 days.

(21) Appl. No.: 17/167,915

(22) Filed: Feb. 4, 2021

(65) Prior Publication Data
US 2021/0395663 A1 Dec. 23, 2021

(30) Foreign Application Priority Data

Jun. 22, 2020 (WO) ............... PCT/CN2020/097536
Aug. 7, 2020 (CN) .......................... 202010788850.8

(51) Int. Cl.
*C12M 3/06* (2006.01)
*C12M 1/12* (2006.01)
*C12M 1/00* (2006.01)

(52) U.S. Cl.
CPC ............ *C12M 27/16* (2013.01); *C12M 23/50* (2013.01); *C12M 37/04* (2013.01); *C12M 41/14* (2013.01)

(58) Field of Classification Search
None
See application file for complete search history.

(56) References Cited

U.S. PATENT DOCUMENTS 5,061,448 A * 10/1991 Mahe ..................... C12M 27/16
422/566
8,822,210 B2 9/2014 Baumfalk et al.
(Continued)

FOREIGN PATENT DOCUMENTS

CN 1954904 A 5/2007
CN 102807953 A 12/2012
(Continued)

OTHER PUBLICATIONS

Document entitled Mechanical Shaker and Fermentation Installation, machine translation of WO 02101000 A2 provided by Clarivate (Year: 2002).*

(Continued)

*Primary Examiner* — Holly Kipouros
(74) *Attorney, Agent, or Firm* — MUNCY, GEISSLER, OLDS & LOWE, P.C.

(57) ABSTRACT

It is described an orbital incubator shaker, which comprises an incubator housing (1) defining an incubation chamber (2), and an orbital shaker (3) configured to shake a shaking table (4). The orbital shaker (3) comprises a drive motor comprising a stator and a rotor (9), and an eccentric bearing mounted to the rotor (9). The orbital shaker (3) is fixed within the incubation chamber (2) or in a mobile version without fixing just being placed inside the incubation chamber (2). The orbital shaker (3) further comprises a bearing (16) configured to support the rotor (9) on a support structure. The rotor (9), the bearing (16) and the support structure are configured to seal the stator from the incubation chamber (2).

14 Claims, 1 Drawing Sheet

(56) References Cited

U.S. PATENT DOCUMENTS

| | | | |
|---|---|---|---|
| 2010/0330663 | A1 | 12/2010 | Baumfalk et al. |
| 2016/0355775 | A1* | 12/2016 | Rahimi ................. C12M 35/04 |
| 2017/0233693 | A1* | 8/2017 | Frei ....................... B01F 31/201 |
| | | | 422/307 |
| 2018/0008943 | A1 | 1/2018 | Corves et al. |
| 2022/0106552 | A1* | 4/2022 | Merk ..................... C12M 41/14 |
| 2022/0228099 | A1* | 7/2022 | Merk ......................... A61L 2/26 |

FOREIGN PATENT DOCUMENTS

| | | | |
|---|---|---|---|
| CN | 103561853 | A | 2/2014 |
| CN | 103591237 | A | 2/2014 |
| CN | 206244809 | U | 6/2017 |
| CN | 106943933 | A | 7/2017 |
| DE | 19814013 | C1 | 7/1999 |
| DE | 102008010780 | B3 | 10/2009 |
| EP | 1626082 | A1 | 2/2006 |
| EP | 1626082 | B1 | 1/2008 |
| EP | 3307059 | A2 | 4/2018 |
| JP | H06178491 | A | 6/1994 |
| JP | 5278861 | B2 | 9/2013 |
| KR | 20030013354 | A | 2/2003 |
| KR | 20130081516 | A * | 7/2013 |
| KR | 20130081516 | A | 7/2013 |
| WO | WO-02101000 | A2 * | 12/2002 ............ C12M 27/16 |
| WO | 2016161155 | A2 | 10/2016 |

OTHER PUBLICATIONS

Document entitled Shaker, machine translation of KR 20130081516 provided by Clarivate (Year: 2013).*

International Search Report of corresponding PCT application (PCT/CN2020/097536) dated Mar. 23, 2021.

Written Opinion of International Searching Authority of corresponding PCT application (PCT/CN2020/097536) dated Mar. 23, 2021.

Search report of corresponding CN priority application (CN202010788850.8) dated Nov. 15, 2021.

First Office Action of corresponding CN application (CN202010788850.8) dated Nov. 23, 2021.

Second Office Action of corresponding CN priority application (CN202010788850.8) dated Feb. 16, 2022.

Third Office Action of corresponding CN priority application (CN202010788850.8) dated May 11, 2022.

Supplementary search report of corresponding CN priority application (CN202010788850.8) dated Jul. 27, 2022.

Notification to Grant Patent Right for Invention of corresponding CN priority application (CN202010788850.8) dated Aug. 5, 2022.

Office Action of corresponding DE application (DE202110110509) dated Mar. 8, 2023.

* cited by examiner

ORBITAL INCUBATOR SHAKERS

CROSS-REFERENCE RELATED APPLICATION

The present application claims the benefit of priority to Patent Cooperation Treaty application number PCT/CN2020/097536, filed on Jun. 22, 2020, titled "INCUBATOR WITH ORBITAL SHAKER", and Chinese patent application No. 202010788850.8, filed on Aug. 7, 2020, titled "INCUBATOR WITH ORBITAL SHAKER," which are incorporated herein by reference in their entirety.

FIELD

The present disclosure relates to orbital incubator shakers, in particular, devices that have functions of an incubator and an orbital shaker.

BACKGROUND

Known orbital shakers are used in laboratory environments to agitate assays or test samples with orbital motion. Orbital incubator shakers include an incubation chamber for keeping biological materials during the agitation at predetermined environmental conditions. Such known orbital incubator shakers provide a wide range of capabilities to meet specific growth requirements by controlling a variety of environmental parameters inside the incubation chamber, such as temperature, relative humidity, carbon dioxide concentration.

All known orbital incubator shakers, however, have certain drawbacks, which prevent optimal usage of a shaking device inside an incubator.

For example, document US 2010/0330663 A1 concerns an incubator with a shaker device. The incubator comprises an incubation chamber for cultivating cells and an adjacent device chamber. A part of the shaker device including a shaking table, a drive arm, a drive shaft and eccentric rotary joints is located inside the incubation chamber, whereas another part of the shaker device including a motor and a drive belt is located in the adjacent device chamber. A base plate seals the incubation chamber from the device chamber. Since some of the parts of the shaking device are located inside the incubation chamber and some are located in the adjacent device chamber, thorough cleaning and disinfection for the parts of the shaking device is cumbersome.

Document EP 1 626 082 B1 concerns a shaking system for a cell culture incubator. The incubator comprises an incubation chamber and a device chamber below the incubation chamber. To shake vessels containing cell cultures in the incubation chamber, an axis, which rotates and performs eccentric movements in a horizontal plane, protrudes into the incubation chamber. At the free end of the axis, a shaking table for holding cell culture vessels is provided. Moreover, in order to enable a shaking movement, the sealing between the incubation chamber and the device chamber is made as an elastic bellows type sealing. However, contamination can get from the device chamber into the incubation chamber due to cracks that may occur over time due the motion of the elastic bellows type sealing.

SUMMARY

The present disclosure provides an orbital incubator shaker which at least partly overcomes the above explained problems.

According to an aspect of the present disclosure, there is provided an orbital incubator shaker comprising an incubator housing defining an incubation chamber, and an orbital shaker configured to shake a shaking table, wherein the orbital shaker comprises a drive motor comprising a stator and a rotor, and an eccentric bearing mounted to the rotor, wherein the orbital shaker is located within the incubation chamber, and the orbital shaker is sealed from the incubation chamber. It will be appreciated that in some embodiments the shaking table is caused to reciprocate eccentrically with the orbital shaker.

BRIEF DESCRIPTION OF THE DRAWINGS

The accompanying drawings are not intended to be drawn to scale. Like reference numbers and designations in the various drawings indicate like elements. For purposes of clarity, not every component can be labeled in every drawing. In the drawings.

DETAILED DESCRIPTION

Figure 1:
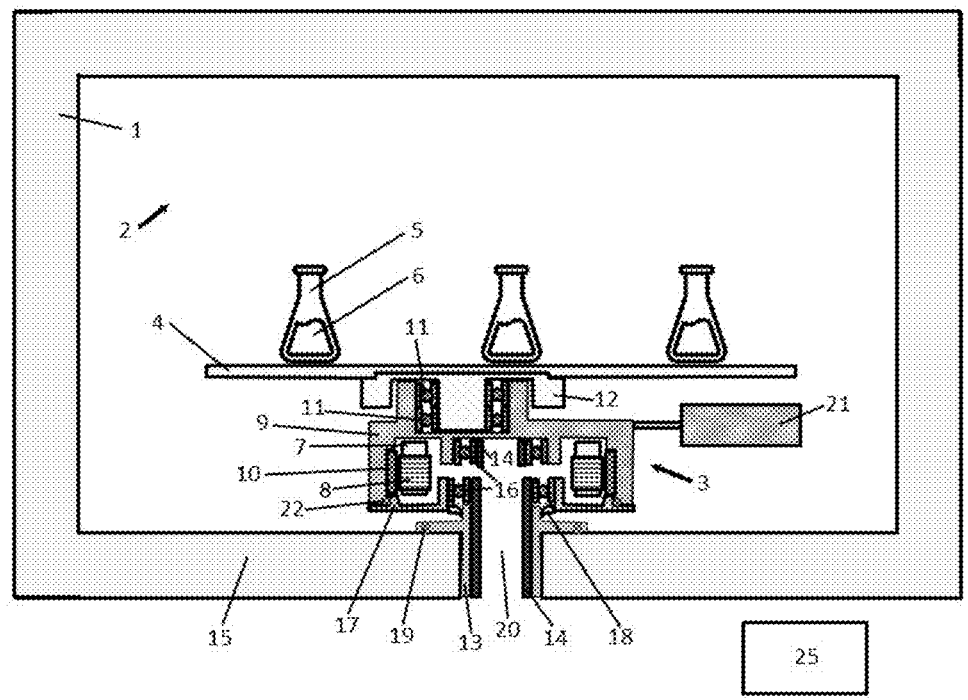
FIG. 1 is a cross-sectional diagram schematically illustrating a first embodiment of an orbital incubator shaker.

Generally, all terms used herein are to be interpreted according to their ordinary meaning in the relevant technical field, unless a different meaning is clearly given and/or is implied from the context in which it is used. All references to a/an/the element, apparatus, component, means, step, etc. are to be interpreted openly as referring to at least one instance of the element, apparatus, component, means, step, etc., unless explicitly stated otherwise. Any feature of any of the embodiments disclosed herein may be applied to any other embodiment, wherever appropriate. Likewise, any advantage of any of the embodiments may apply to any other embodiments, and vice versa. Other objectives, features and advantages of the enclosed embodiments will be apparent from the following description.

Some of the embodiments contemplated herein will now be described more fully with reference to the accompanying drawings. Other embodiments, however, are contained within the scope of the subject matter disclosed herein, the disclosed subject matter should not be construed as limited to only the embodiments set forth herein. Rather, these embodiments are provided by way of example to convey the scope of the subject matter to those skilled in the art.

According to an aspect of the present disclosure, there is provided an orbital incubator shaker comprising an incubator housing defining an incubation chamber, and an orbital shaker configured to shake a shaking table, wherein the orbital shaker comprises a drive motor comprising a stator and a rotor, and an eccentric bearing mounted to the rotor, wherein the orbital shaker is located within the incubation chamber, and the orbital shaker is sealed from the incubation chamber. It will be appreciated that in some embodiments the shaking table is caused to reciprocate eccentrically with the orbital shaker.

The incubation chamber may be a kind of closed or closable chamber that enables keeping biological materials during agitation at predetermined environmental conditions. For example, the incubation chamber may be used for mammalian cell culturing. The shaking table may be placed in a fixed manner on the eccentric bearing. On the shaking table, a plurality of containers, for example, Erlenmeyer flasks, storing biological material may be releasable fixed and agitated.

The eccentric bearing may guide the shaking table to be moved in elliptical orbits, in particular, in varying elliptical orbits. For this, the eccentric bearing may comprise closed ball bearings. The eccentric bearing may also comprise a mechanical guidance to provide the orbital motion with forced rotation. The eccentric bearing may be mounted in a fixed manner to the rotor. It is also possible that the location of the eccentric bearing on the rotor can be changed to different positions so that the shaking diameter of the orbital motions may be changed. For this, a locking means for shifting and fixing the position of the eccentric bearing on the rotor may be provided. The locking means may comprise a slide rail arrangement, a screw connection arrangement or the like, to enable releasable fixation of the eccentric at different positions on the rotor.

Due to structure of the eccentric bearing being mounted to the rotor and the orbital shaker being fixed within the incubation chamber or in a mobile version being placed inside the incubation chamber, a compact design with a relatively small height difference between the drive motor and the shaking table is provided, which also helps to prevent strong vibrations at the shaking table.

The orbital shaker may comprise a support structure configured to support the orbital shaker on a base of the incubator housing such that the orbital shaker extends to the inside of the incubation chamber. In a non-mobile version of the orbital shaker, the orbital shaker may comprise a fixture configured to fix the orbital shaker to a base of the incubator housing such that the orbital shaker extends to the inside of the incubation chamber. Preferably, the orbital shaker may be directly fixed to the base of the incubator housing without an additional base plate being provided between the orbital shaker and the base of the incubator housing.

In a mobile version, the orbital shaker can also be placed inside an incubator without being fixed to the base of the incubator housing. In this case, the orbital shaker may comprise a stand configured to hold the orbital shaker on the base of the incubator housing.

To prevent a loss of cell cultures due to contamination, it is important to efficiently clean, disinfect and decontaminate the incubation chamber, i.e., all surfaces within the incubation chamber. For example, this is essential for a Good-Manufacturing-Practice—(GMP) compliant cell cultivation. Moreover, a precisely controlled climate in the incubation chamber is necessary to maintain optimal cell culture conditions. To fulfill these requirements, the orbital shaker may comprise a bearing configured to support the rotor on the fixture or on the stand, wherein the rotor, the bearing, and the fixture or stand are configured to seal the stator from the incubation chamber. Preferably, the bearing comprises a ball bearing. Thus, the orbital shaker, i.e., the stator, is fully encapsulated, and the fully encapsulated orbital shaker is located inside the incubation chamber. In particular, except some part of the fixture in the non-mobile version of the orbital shaker, the orbital shaker may be completely located inside the incubation chamber. Thus, on the one hand, the sealing of the stator from the incubation chamber by means of the rotor, the bearing, and the fixture or stand helps to provide surfaces within the incubation chamber that can be easily cleaned, disinfected and decontaminated. On the other hand, the sealing of the heat-generating stator from the incubation chamber helps to facilitate controlling the temperature in the incubation chamber.

In order to improve the sealing of the stator from the incubation chamber, the rotor may comprise a rotor plate, and the bearing may be a sealed bearing located between the rotor plate and the fixture, or between the rotor plate and the stand. Preferably, the sealed bearing comprises a sealed ball bearing. By means of the sealed bearing, penetration of any moving part of the orbital shaker into the incubation chamber can be prevented. Moreover, the rotor plate may be screwed to the rotor and the sealed bearing may comprise a bearing isolator having a labyrinth seal design to enable sealing of the stator from the incubation chamber and additionally prevent lubricant leakage from the bearing into the incubation chamber.

Additionally or alternatively to the sealed bearing, the orbital shaker may comprise another dynamic seal. In this embodiment, the rotor, the dynamic seal, and the fixture or stand are configured to seal the stator from the incubation chamber. The dynamic seal may be configured such that it retains or separates moisture and fluids, keeps out contaminants, and contains temperature and climate in the incubation chamber. Moreover, it creates a barrier between moving and stationary surfaces in the rotary orbital shaker. The dynamic seal may be a contact seal bearing the seal against a mating surface under positive pressure, or a clearance seal operating with positive clearance so that there is no rubbing contact.

In one embodiment, the dynamic seal comprises a lip seal mounted on the rotor. The lip seal may be a flexible lip and may point towards the incubation chamber to ensure keeping the incubation chamber clean and decontaminated. The dynamic seal may further comprise a spring helping to keep the lip seal in contact with the fixture or stand. Preferably, the lip seal is an U.S. Food and Drug Administration—(FDA) approved tight-seal.

In a further embodiment of the non-mobile version of the orbital shaker, the fixture may comprise a bushing and a shaft, wherein the bushing is mounted to the incubator housing and the bearing is mounted to the shaft. Preferably, the shaft is a hollow shaft.

In another embodiment of the mobile version of the orbital shaker, the stand may comprise a base element and a shaft, wherein the base element is placed on the bottom of the incubator housing and the bearing is mounted to the shaft. Preferably, the shaft is a hollow shaft.

To improve the sealing of the stator from the incubation chamber in the non-mobile version of the orbital shaker, a static sealing, e.g., an O-ring, may be provided which seals the bushing to the incubator housing.

In a preferred embodiment, the drive motor is a direct drive motor, in particular, a rotary direct drive motor. The rotary drive motor may be a torque motor. The stator of the direct drive motor may comprise direct current electro magnets and sensors, and the rotor may comprise at an inner circumferential surface permanent magnets. The electro magnets of the stator may by switched by a control unit (e.g., a microprocessor) depending on the position of the rotor determined by the sensors. Since the rotary direct drive motor does not comprise any mechanical power transfer means (for example, a belt), there is close to no abrasion. Moreover, rotary direct drive motors provide the advantages of low noise, low power consumption, and low heat generation. Furthermore, since the motor speed of the rotary direct drive motor is the same as the shaking speed of the shaking table, the control unit may easily change the shaking diameter of the shaking table. Specifically, the rotary direct drive motor ensures a high performing rotary movement regarding shaking speed (rpm) and load (kg) of the shaking table.

To enable discharge of heat generated by the drive motor, the orbital shaker in the non-mobile version of the orbital shaker may further comprise a passage extending through the base of the incubator housing. Preferably, the passage may extend through the hollow shaft between the stator and an outside of the incubation chamber so that heat generated by the drive motor may be discharged to the outside. For improved heat discharging, there may be provided a ventilator.

The orbital shaker may further comprise a cooling channel within the passage. The cooling channel may be configured such that a cooling liquid may stream there through. In particular, the stator may be used as a heat sink through active cooling with liquid from the cooling channel.

To compensate centrifugal forces created by liquid masses stored in containers fixed on the shaking table, the orbital shaker may further comprise an adjustable counterweight mounted to the rotor. For example, the adjustable counterweight may be screwed to the rotor. The counterweight allows manual calibration in case of imbalance situations so that liquid stored in the containers may be shaken at high speed. The counterweight may also be adjusted in accordance with a shifting of the location of the eccentric bearing on the rotor.

Preferably, a diameter of the orbital movement of the shaking table may be between 19 and 50 mm. Further preferably, the rotation speed of the shaking table may be between 80 and 200 rpm with a maximum rotation speed of 400 rpm. Further preferably, the load to be shaken may be up to 25 kg.

To ensure corrosion resistance, chemical resistance and easy cleaning of all surfaces within the incubation chamber, at least one of the rotor, the counterweight and an inside of the incubation chamber is made of stainless steel.

On the shaking table, one or more Erlenmeyer flasks, for instance 1 to 15 Erlenmeyer flasks, which may be up to 365 mm in height and may contain between 10 ml and 3000 ml of liquid, may be fixed in a releasable manner. To absorb respective lever forces during shaking, the eccentric bearing may comprise two sealed bearings that are stacked above each other. In addition, the shaking table may be mechanically guided so that it performs an orbital movement instead of a circular movement. Alternatively, such stable movement may be obtained with two pairs of leaf springs.

FIG. 1 is a cross-sectional diagram schematically illustrating a first embodiment of an orbital incubator shaker. FIG. 1 is a cross-sectional diagram schematically illustrating a first embodiment of an orbital incubator shaker. The orbital incubator shaker comprises an incubator having an incubator housing 1 defining an incubation chamber 2 and an orbital shaker 3. The orbital shaker 3 may be sealed from the incubation chamber 2 to prevent foreign substances in the incubation chamber 2 from entering the inside of the orbital shaker 3. The incubator may comprise further elements for operating the incubator which are not shown in FIG. 1, for example, a separate heating device for heating the air, fans that suck air into the incubation chamber 2 and other arrangements forcing the air to circulate throughout the whole chamber, temperature and climate control means, a user interface, etc.

On the orbital shaker 3, a shaking table 4 is releasable fixed. On top of the shaking table 4, three Erlenmeyer flasks 5 are releasable fixed. Within each Erlenmeyer flask 5, a biological liquid 6 is stored. When the shaking table 4 is shaken by the orbital shaker 3, the biological liquid 6 is shaken.

The orbital shaker 3 is fixed to the bottom 15 of the incubator housing 1, and is located inside the incubation chamber 2.

The orbital shaker 3 comprises a drive motor, an eccentric bearing, an adjustable counterweight 21, a fixture for fixing the orbital shaker 3 to the bottom 15 of the incubator housing 1, two bearings 16, and a lip seal 18. FIG. 1 further shows a control unit 25 which controls the drive motor.

The drive motor is a rotary direct drive motor and comprises a stator, and a rotor 9. The stator comprises a plurality of axis elements 7 around which magnetic coils 8 are wound, and which act as electro magnets. At an inner circumferential surface of the rotor 9, a plurality of permanent magnets 10 are disposed. Furthermore, sensors (not shown in FIG. 1) for determining the position of the rotor 9 are provided. Depending on the determined positions of the rotor 9, the control unit 25 controls electric currents supplied to the magnetic coils 8 in order to rotate the rotor 9. The control unit 25 may be communicatively connected to the magnetic coils 8 and the sensors for determining the position of the rotor 9 through the passage 20.

Attached (for example, screwed) to the bottom of the rotor 9 is a rotor plate 17. The rotor 9 and the rotor plate 17 surround the axis elements 7, the magnetic coils 8 and the permanent magnets 10. The rotor plate 17 also supports the permanent magnets 10. For sealing the bottom of the rotor 9 to the rotor plate 17, an O-ring 22 is provided between the rotor 9 and the rotor plate 17.

The fixture 13 and 14 comprises a bushing 13 and a hollow shaft 14. The bushing 13 has a cross sectional double-T-shape and is fixed (for example screwed) to the bottom 15 of the incubator housing 1. The bottom 15 of the incubator housing 1 comprises an opening through which the bushing 13 extends. In particular, the bushing 13 is attached to the inner walls of the opening. Thus, the bushing 13 extends inside the incubation chamber 2 and in the opening at the bottom 15 of the incubator housing 1. Additionally, the bushing 13 may extend to the outside of the incubation chamber 2 (not shown in FIG. 1). For sealing the bushing 13 to the bottom 15 of the incubator housing 1, an O-ring 19 is provided at the bushing 13. The O-ring 19 is in contact with an inner surface of the bottom 15 of the incubator housing 1.

Attached to the bushing 13 is the hollow shaft 14. The hollow shaft 14 has a cylindrical shape. At outer circumferential surfaces of the hollow shaft 14, two ball bearings 16 are mounted. The hollow shaft 14 extends from an upper surface of the rotor 9 to the opening at the bottom 15 of the incubator housing 1. Additionally, the hollow shaft 14 may extend to the outside of the incubation chamber 2 (not shown in FIG. 1). The rotor 9 with the attached rotor plate 17 is supported by the two ball bearings 16 and is configured to be rotated around the hollow shaft 14.

Attached to the rotor 9 (for example, screwed to the rotor 9) is the counterweight 21. The counterweight 21 is adjustable in that its distance from the rotor 9 may be manually adjusted in order to counter imbalances due to heavy loads (for instance, Erlenmeyer flasks 5 and biological liquid 6) placed on the shaking table 4, so as to inhibit or eliminate strong vibration of the orbital shaker 3.

The eccentric bearing comprises two ball bearings 11 stacked upon each other and an eccentric 12. The rotor 9 comprises at its upper end a tray-shaped part. The two ball bearings 11 are mounted inside the tray-shaped part. The eccentric 12 comprises an inner shaft having a cylindrical shape which is supported inside the two ball bearings 11 so that it may be rotated. Additionally, the eccentric 12 mechanically guides the shaking table 4 such that it moves in orbital motions. The eccentric 12 covers an upper part of the rotor 9 and the ball bearings 11. On top of the eccentric 12, the shaking table 4 is placed. The shaking table 4 may be releasable fixed to the eccentric 12. For example, an underside of the shaking table 4 may be provided with a recess to accommodate an upper surface of the eccentric 12. It will be appreciated that the eccentric 12 is located off-center of the shaking table 4.

In another embodiment (not shown in FIG. 1), a locking means may be provided at the eccentric 12, which enable the eccentric 12 to be moved to and locked at different positions to the left and/or right in the horizontal plane. Thereby, the shaking diameter of the orbital motions may be changed. The locking means may comprise a slide rail arrangement, a screw connection arrangement or the like, as long as it enables releasable fixation of the eccentric 12 at different positions on the rotor 9. Additionally, the counterweight 21 may be adjusted at the same time.

All ball seals are 11 and 16 are sealed ball bearings. Thus, the bushing 13, the O-ring 19, the hollow shaft 14, the sealed ball bearing 16, the rotor plate 17, the O-ring 22, and the rotor 9 fully encapsulate the stator from the incubation chamber 2. It will be appreciated that the bearings 11 and 16 may be cylindrical roller bearings in addition to ball bearings.

Additionally, the lip seal 18 provides a sealing between the bushing 13 and the rotor plate 17. The lip seal 18 is a flexible FDA-approved tight-seal and is mounted on the rotor plate 17. The lip seal 18 points towards the bushing 13 into the incubation chamber 2, which helps to keep the incubation chamber 2 clean and decontaminated. More precisely, the lip seal 18 is fixed at one end to the rotor plate 17 and extends at the other end downwards in the direction of bushing 13 until it abuts bushing 13.

The lip seal 18 may also be used in an embodiment where the ball bearing 16 is no sealed ball bearing 16 but only a normal ball bearing. In this case, the bushing 13, the O-ring 19, the lip seal 18, the rotor plate 17, the O-ring 22, and the rotor 9 seal and fully encapsulate the stator from the incubation chamber 2, preventing substance within the incubation chamber 2 from contacting with the stator.

Moreover, in another embodiment, the lip seal 18 may be omitted and only the bushing 13, the O-ring 19, the hollow shaft 14, the sealed ball bearing 16, the rotor plate 17, the O-ring 22, and the rotor 9 fully encapsulate the stator from the incubation chamber 2. This embodiment has the advantage that no moving part of the orbital shaker 3 penetrates into the incubation chamber 2.

In order to facilitate cleaning, disinfection and decontamination of the orbital incubator shaker, the inner surface of the incubator housing 1, the rotor 9, the counterweight 21, the hollow shaft 14 and/or the bushing 13 may be made of stainless steel. Moreover, the outer surface of the incubator housing 1 or the entire incubator housing 1 may be made of stainless steel. Additionally, the surfaces of the orbital shaker 3 facing the incubation chamber 2 may be designed such that no hidden vaults or dead spaces are present. Specifically, all connections of the elements of the orbital shaker 3 are not only covered but also sealed. In particular, the orbital shaker 3 is designed to comply with the norm ISO 14159:2002 "Safety of machinery—Hygiene requirements for the design of machinery" such that all parts inside the incubation chamber 2 are accessible for cleaning and disinfection.

Inside the hollow shaft 14, a passage 20 is provided. The passage 20 extends between the stator and the outside of the incubator housing 1. In particular, the passage 20 extends from the stator between the two ball bearings 16 to the outside of the incubator housing 1. By means of the passage 20, heat generated by the drive motor may be discharged to the outside of the incubator housing 1.

Additionally, a cooling channel (not shown in FIG. 1) may be provided in the passage 20. In particular, the cooling channel may extend between the stator and the outside of the incubator housing 1. Within the cooling channel, a liquid can flow which helps to discharge heat generated by the drive motor to the outside of the incubator housing 1.

The above described embodiments provide the following advantages:

The orbital incubator shaker is designed in accordance with known hygienic design principles. The choice of material, surface quality and the absence of cavities allow for easy and thorough cleaning, disinfection and decontamination of the orbital incubator shaker, which allows GMP-compliant cell cultivation.

The encapsulation of the orbital shaker 3 protects the stator and all electronic parts from moisture and microbial contamination as well as from chemicals used for cleaning, disinfection and decontamination of the orbital incubator shaker.

Except the lip seal 18, no rotating part penetrates into the incubation chamber 2.

The orbital shaker 3 has a simple and clean design, and the orbital shaker 3 may be easily dismantled, replaced and/or repaired.

The direct drive motor has a low net energy consumption leading to low heat emission.

A small height difference between the direct drive motor and the load leads to reduced vibrations.

Figure 2:
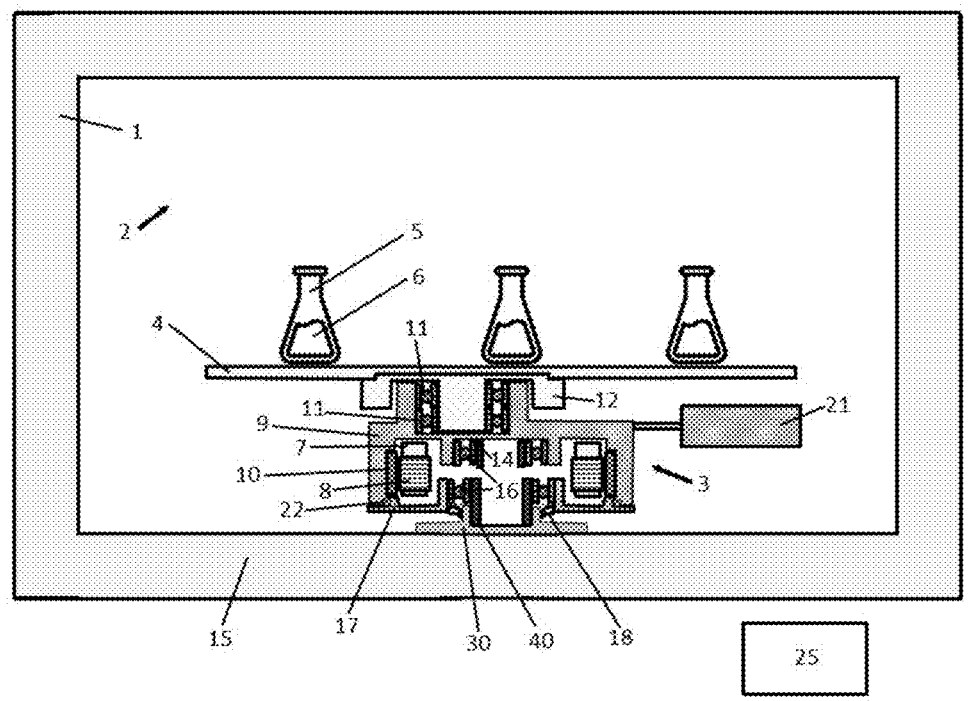
FIG. 2 is a cross-sectional diagram schematically illustrating a second embodiment of an orbital incubator shaker.

FIG. 2 is a cross-sectional diagram schematically illustrating a second embodiment of an orbital incubator shaker.

The orbital incubator shaker shown in FIG. 2 differs from the orbital incubator shaker shown in FIG. 1 in that the incubator housing 1 does not have any opening at its bottom 15. Moreover, instead of the bushing 13, there is provided a base element 30, and the hollow shaft 40 only extends from the rotor 9 to a top of the base element 30. Also, the O-ring 19 is not necessary. All other elements are the same and have the same or similar functions. Thus, they are not explained again.

The encapsulated orbital shaker 3 shown in FIG. 2 may be placed in and removed from the incubation chamber 2. In particular, the orbital shaker 3 may be placed with the base element 30 on the bottom 15 of the incubator housing 1 without being fixed to the bottom 15 of the incubator housing 1. The base element 30 seals the lower part of the orbital shaker 3. The base element 30 may be made of stainless steel. The function of the hollow shaft 40 is the same as the function of the hollow shaft 14. Moreover, the base element 30 and the hollow shaft 40 may be made as one piece.

What is claimed is:
1. An orbital incubator shaker, comprising:
   an incubator housing (1) defining an incubation chamber (2), and
   an orbital shaker (3) configured to shake a shaking table (4), wherein the orbital shaker (3) comprises
      a drive motor comprising a stator and a rotor (9), an eccentric bearing mounted to the rotor (9), a support structure configured to support the orbital shaker (3) on a base (15) of the incubator housing (1) such that the orbital shaker (3) extends to the inside of the incubation chamber (2), wherein the support structure is implemented as a fixture configured to fix the orbital shaker (3) to a base (15) of the incubator housing (1) or a stand configured to hold the orbital shaker (3) on the base (15) of the incubator housing (1), and a bearing (16) configured to support the rotor (9) on the fixture or on the stand, wherein the orbital shaker (3) is located within the incubation chamber (2), and the stator is sealed from the incubation chamber (2), the rotor (9), the bearing (16), and the fixture or stand are configured to seal the stator from the incubation chamber (2).

2. The orbital incubator shaker of claim 1, wherein the rotor (9) comprises a rotor plate (17), wherein the bearing (16) is a sealed bearing located between the rotor plate (17) and the fixture, or between the rotor plate (17) and the stand.

3. The orbital incubator shaker of claim 1, wherein the orbital shaker (3) further comprises:

a dynamic seal (18), wherein the rotor (9), the dynamic seal (18), and the fixture or stand are configured to seal the stator (7, 8) from the incubation chamber (2).

4. The orbital incubator shaker of claim 3, wherein the dynamic seal (18) comprises a lip seal mounted on the rotor (9).

5. The orbital incubator shaker of claim 1, wherein the fixture comprises a bushing (13) and a shaft (14), wherein the bushing (13) is mounted to the incubator housing (1) and the bearing (16) is mounted to the shaft (14).

6. The orbital incubator shaker of claim 5, further comprising an O-ring (19) configured to seal the bushing (13) to the incubator housing (1).

7. The orbital incubator shaker of claim 5, wherein the fixture further comprises a passage (20) inside the shaft (14) extending through the base (15) of the incubator housing (1).

8. The orbital incubator shaker of claim 7, wherein the passage (20) extends between the stator and an outside of the incubation chamber (2).

9. The orbital incubator shaker of claim 8, further comprising:

a cooling channel within the passage (20), wherein the cooling channel is configured such that a cooling liquid may stream there through.

10. The orbital incubator shaker of claim 7, further comprising:

a cooling channel within the passage (20), wherein the cooling channel is configured such that a cooling liquid may stream there through.

11. The orbital incubator shaker of claim 1, wherein the drive motor is a rotary direct drive motor.

12. The orbital incubator shaker of claim 1, further comprising:

an adjustable counterweight (21) mounted to the rotor (9).

13. The orbital incubator shaker of claim 12, wherein at least one of the rotor (9), the counterweight (21) and an inside of the incubation chamber (2) is made of stainless steel.

14. The orbital incubator shaker of claim 1, wherein the eccentric bearing comprises two sealed bearings (11) that are stacked above each other.

\* \* \* \* \*